US00PP19676P2

(12) United States Plant Patent
Bergman

(10) Patent No.: US PP19,676 P2
(45) Date of Patent: Feb. 10, 2009

(54) ***CHRYSANTHEMUM* PLANT NAMED 'REGAL YOIRVINE'**

(50) Latin Name: *Chrysanthemum×morifolium*
Varietal Denomination: Regal Yoirvine

(75) Inventor: Wendy R. Bergman, Lehigh Acres, FL (US)

(73) Assignee: Yoder Brothers Inc., Barberton, OH (US)

( * ) Notice: Subject to any disclaimer, the term of this patent is extended or adjusted under 35 U.S.C. 154(b) by 0 days.

(21) Appl. No.: 11/983,732

(22) Filed: Nov. 12, 2007

(51) Int. Cl.
*A01H 5/00* (2006.01)

(52) U.S. Cl. ..... Plt./286

(58) Field of Classification Search ..... Plt./286, Plt./297

See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Chrysanthemum* plant named 'Regal Yoirvine', characterized by its upright and uniformly mounded plant habit; freely branching and vigorous growth habit; dark green-colored foliage; uniform flowering response; early and freely flowering habit; daisy-type inflorescences with purple-colored ray florets; and excellent post-production longevity with inflorescences maintaining good substance and color for about four weeks in an interior environment.

1 Drawing Sheet

Botanical designation: *Chrysanthemum×morifolium.*
Cultivar denomination: 'Regal Yoirvine'.

Cross-referenced to related applications:

*Chrysanthemum* Plant Named Currant Yoirvine; Wendy R. Bergman, applicant; filed concurrently (U.S. Plant Patent application Ser. No. 11/983,744).

*Chrysanthemum* Plant Named Dark Bronze Yoirvine; Wendy R. Bergman, applicant; filed concurrently (U.S. Plant Patent application Ser. No. 11/983,733).

BACKGROUND OF THE INVENTION

The present invention relates to a new and distinct cultivar of *Chrysanthemum* plant, botanically known as *Chrysanthemum×morifolium,* commercially grown as a pot-type *Chrysanthemum* and hereinafter referred to by the name 'Regal Yoirvine'.

The new *Chrysanthemum* is a naturally-occurring whole plant mutation of the *Chrysanthemum×morifolium* cultivar Yoirvine, not patented. The new *Chrysanthemum* was discovered and selected by the Inventor as a single flowering plant within a population of plants of the cultivar Yoirvine in December, 2003, in Fort Myers, Fla. in a controlled greenhouse environment. The selection of this plant was based on its uniform plant growth habit, vigor, freely branching habit, desirable inflorescence form and floret colors, fast response time and excellent postproduction longevity Asexual reproduction of the new *Chrysanthemum* by vegetative tip cuttings was first conducted in Fort Myers, Fla. in March, 2004. Asexual reproduction by cuttings has shown that the unique features of this new *Chrysanthemum* are stable and reproduced true to type in successive generations.

SUMMARY OF THE INVENTION

Plants of the cultivar Regal Yoirvine have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Regal Yoirvine'. These characteristics in combination distinguish 'Regal Yoirvine' as a new and distinct pot-type *Chrysanthemum* cultivar:

1. Upright and uniformly mounded plant habit.
2. Freely branching and vigorous growth habit.
3. Dark green-colored foliage.
4. Uniform flowering response.
5. Typically grown as a natural spray type.
6. Early flowering habit, eight-week response time.
7. Freely flowering habit.
8. Daisy-type inflorescences with purple-colored ray florets.
9. Excellent postproduction longevity with inflorescences maintaining good substance and color for about four weeks in an interior environment.

Plants of the new *Chrysanthemum* differ from plants of the percent, the cultivar Yoirvine, in the following characteristics:

1. Plants of the new *Chrysanthemum* are more uniform and flower more uniformly than plants of the cultivar Yoirvine.
2. Plants of the new *Chrysanthemum* and the cultivar Yoirvine differ in ray floret color as plants of the cultivar Yoirvine have light purple-colored ray florets.

Plants of the new *Chrysanthemum* differ from plants of the cultivars Currant Yoirvine and Dark Bronze Yoirvine primarily in ray floret color.

Plants of the new *Chrysanthemum* can be compared to plants of the *Chrysanthemum* cultivar Yorockport, disclosed in U.S. Plant Pat. No. 17,475. In side-by-side comparisons conducted in Fort Myers, Fla., plants of the new *Chrysanthemum* differed from plants of the cultivar Yorockport in the following characteristics:

1. Plants of the new *Chrysanthemum* were more vigorous than plants of the cultivar Yorockport.
2. Inflorescences of plants of the new *Chrysanthemum* and the cultivar Yorockport differed in ray floret color as plants of the cultivar Yorockport had darker purple-colored ray florets.

BRIEF DESCRIPTION OF THE PHOTOGRAPH

The accompanying photograph illustrates the overall appearance of the new *Chrysanthemum*. This photograph shows the colors as true as it is reasonably possible to obtain in colored reproductions of this type. Colors in the photograph may differ slightly from the color values cited in the detailed botanical description which accurately describe the colors of the new *Chrysanthemum*. The photograph comprises a side perspective view of typical flowering platns of 'Regal Yoirvine' grown in a container.

DETAILED BOTANICAL DESCRIPTION

The aforementioned photographs and following observations and measurements describe plants grown in Leamington, Ontario, Canada during the summer in a glass-covered greenhouse and under conditions and practices which approximate those generally used in commercial pot-type *Chrysanthemum* production. During the production of the plants, day temperatures ranged from about 21° C. to 27° C., night temperatures ranged from about 17° C. to 19° C. and light levels ranged from 4,000 to 6,000 foot candles. Four unrooted cuttings were directly stuck in 15-containers, exposed to long day/short night conditions, and pinched about three weeks later. At the time of the pinch, the photoinductive short day/long night treatments were started. Plants used in the photographs and for the description were center-budded and were about eleven weeks old. In the following description, color references are made to The Royal Horticultural Society Colour Chart, 1995 Edition, except where general terms of ordinary dictionary significance are used.

Botanical classification: *Chrysanthemum×morifolium* cultivar Regal Yoirvine.

Parentage: Naturally occurring whole plant mutation of the *Chrysanthemum×morifolium* cultivar Yoirvine, not patented.

Propagation:

*Type.*—Terminal vegetative cuttings.

*Time to initiate roots.*—About four days at temperatures of about 21° C.

*Time to produce a rooted young plant.*—About ten days at temperatures of about 21< C.

*Root description.*—Fine to thick, fibrous; white in color.

*Rooting habit.*—Freely branching; moderately dense.

Plant description:

*Appearance.*—Herbaceous daisy pot-type *Chrysanthemum* typically grown as a center-budded or as a natural spray type. Stems upright and outwardly spreading giving a uniformly mounded appearance to the plant. Freely branching habit, about four to five lateral branches develop after removal of terminal apex (pinching); dense and full plant habit. Strong and vigorous growth habit.

*Plant height.*—About 28 cm.

*Plant width.*—About 44 cm.

*Lateral branches.*—Length: About 24 cm. Diameter: About 6 mm. Internode length: About 2 cm. Strength: Strong Texture: Pubescent. Color: Between 144A and 146B.

Foliage description:

*Arrangement.*—Alternate, simple.

*Length.*—About 7.5 cm.

*Width.*—About 5.4 cm.

*Shape.*—Palmately lobed.

*Apex.*—Cuspidate to mucronate.

*Base.*—Attenuate with truncate tendencies.

*Margin.*—Palmately lobed, sinuses between lateral lobes parallel to divergent.

*Texture, upper and lower surfaces.*—Fine pubescence; veins prominent on lower surface.

*Color.*—Developing leaves, upper surface: Darker than 147A. Developing leaves, lower surface: Darker than 147B. Fully expanded leaves, upper surface: Close to 147A; venation, close to 147A to 147B. Fully expanded leaves, lower surface: Close to 147B; venation, close to 147B.

*Petiole.*—Length: About 1.6 cm. Diameter: About 5 mm. Texture, upper and lower surfaces: Pubescent. Color, upper surface: Close to 147B. Color, lower surface: Close to 147B to 147C.

Inflorescence description:

*Appearance.*—Daisy-type inflorescence form with elongated oblong-shaped ray florets. Inflorescences borne on terminals above foliage. Disk and ray florets arranged acropetally on a capitulum. Inflorescence not fragrant. Typically grown as a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about eight weeks later.

*Postproduction longevity.*—Inflorescences maintain good color and substance for about four weeks in an interior environment.

*Quantity of inflorescences.*—Freely flowering, about 15 inflorescences develop per lateral stem.

*Inflorescence bud.*—Height: About 6 mm. Diameter: About 8 mm. Shape: Oblate. Color: Close to 147A.

*Inflorescence size.*—Diameter: About 7.5 cm. Depth (height): About 1.25 cm. Diameter of disc: About 1.1 cm. Receptacle height: About 6 mm. Receptacle diameter: About 6 mm. Receptacle color: Close to 144B.

*Ray florets.*—Shape: Elongated oblong. Orientation: Initially upright, then with development, close to perpendicular from vertical. Aspect: Initially incurved, then mostly flat. Length: About 3.4 cm. Width: About 1 cm. Apex: Acute. Base: Attenuate; short corolla tube. Margin: Entire. Texture, upper and lower surfaces: Smooth, glabrous; satiny. Number of ray florets per inflorescence: About 32 arranged in about two or three whorls. Color: When opening and fully opened, upper surface: Close to 155D overlain with close to 71A. When opening and fully opened, lower surface: Close to 155D underlain with close to between 71A and 77A.

*Disc florets.*—Arrangement: Massed at center of receptacle. Shape: Tubular, elongated. Apex: Five-pointed. Length: About 4 mm. Width: About 1 mm. Number of disc florets per inflorescence: About 175. Color, immature: Apex: Close to 154B. Mid-section and base: Close to 155D. Color, mature: Apex: Close to 6A. Mid-section: Close to 154A. Base: Close to 155D.

*Phyllaries.*—Number of phyllaries per inflorescence: About 16 arranged in about two whorls. Length: About 9 mm. Width: About 3 mm. Shape: Lanceolate. Apex: Acute. Base: Truncate. Margin: Entire. Texture, upper surface: Smooth, waxy. Texture, lower surface: Pubescent. Color, upper surface: Close to 146A. Color, lower surface: Close to 147A.

*Peduncles.*—Length: First peduncle: About 5.5 cm. Fourth peduncle: About 7.5 cm. Seventh peduncle: About 11 cm. Diameter (first peduncle): About 2.5 mm. Angle: About 45° from vertical. Strength: Strong, flexible. Texture: Pubescent. Color: Close to between 144A to 146B.

*Reproductive organs.*—Androecium: Present on disc florets only. Stamen length: About 4 mm. Filament length: About 3 mm. Filament color: Close to 154D. Anther shape: Narrowly oblong. Anther length: Less than 1 mm. Anther color: Close to 6A. Pollen amount: None observed. Gynoecium: Present on both ray and disc florets. Pistil length: About 5 mm. Stigma shape: Bi-parted. Stigma color: Close to 4A. Style length: About 4 mm. Style color: Close to 4A. Ovary color: Close to 155D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 38° C.

It is claimed:

1. A new and distinct *Chrysanthemum* plant named 'Regal Yoirvine' as illustrated and described.

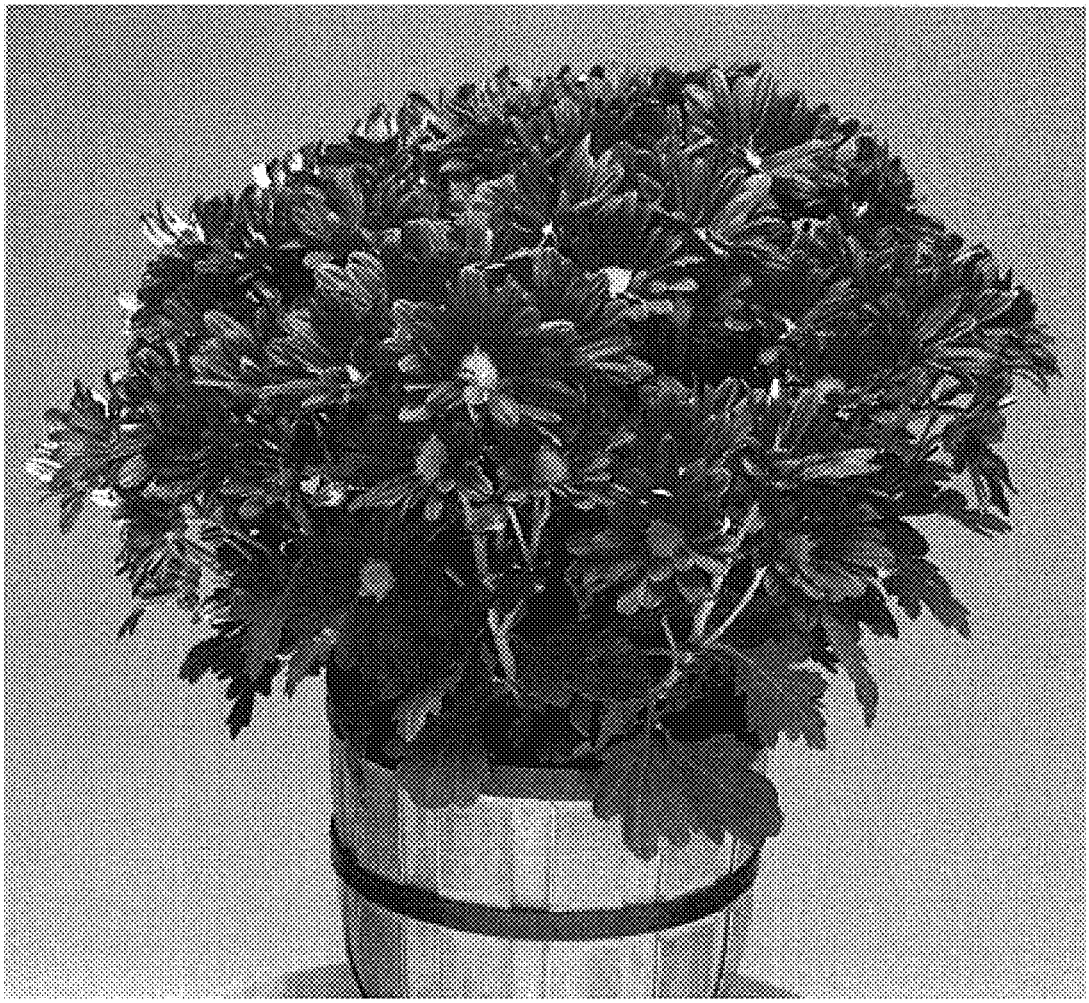

* * * * *